(12) United States Patent
Magagnoli

(10) Patent No.: US 11,399,947 B2
(45) Date of Patent: Aug. 2, 2022

(54) MODULAR SPACER DEVICE FOR THE JOINTS OF THE HUMAN BODY

(71) Applicant: COSSINGTON LIMITED, Kingston upon Thames (GB)

(72) Inventor: Augusto Magagnoli, Cervia (IT)

(73) Assignee: COSSINGTON LIMITED, Kingston upon Thames (GB)

( * ) Notice: Subject to any disclaimer, the term of this patent is extended or adjusted under 35 U.S.C. 154(b) by 95 days.

(21) Appl. No.: 16/317,769

(22) PCT Filed: Jul. 18, 2017

(86) PCT No.: PCT/IB2017/054331
§ 371 (c)(1),
(2) Date: Mar. 25, 2019

(87) PCT Pub. No.: WO2018/015878
PCT Pub. Date: Jan. 25, 2018

(65) Prior Publication Data
US 2020/0179125 A1 Jun. 11, 2020

(30) Foreign Application Priority Data
Jul. 20, 2016 (IT) .......................... 102016000075924

(51) Int. Cl.
*A61F 2/38* (2006.01)
*A61F 2/30* (2006.01)
(52) U.S. Cl.
CPC ............ *A61F 2/3859* (2013.01); *A61F 2/389* (2013.01); *A61F 2/3836* (2013.01);
(Continued)

(58) Field of Classification Search
CPC .................. A61F 2/3859; A61F 2/389; A61F 2002/30604; A61F 2002/30316;
(Continued)

(56) References Cited

U.S. PATENT DOCUMENTS 4,209,861 A * 7/1980 Walker .................. A61F 2/3886
623/20.27
5,152,797 A * 10/1992 Luckman ............ A61F 2/30734
623/20.16
(Continued)

FOREIGN PATENT DOCUMENTS

EP 2254519 12/2010
WO 2005037147 4/2005
(Continued)

*Primary Examiner* — Yashita Sharma
*Assistant Examiner* — Melissa A Hoban
(74) *Attorney, Agent, or Firm* — Themis Law

(57) ABSTRACT

A modular spacer device for a knee joint includes a tibial element adapted to be constrained to an end of the tibial bone and a femoral element adapted to be constrained to an end of the femoral bone and to be articulated on the tibial element. The tibial element has first and second surfaces opposite to each other, and the femoral element has first surface and second surfaces opposite to each other. The first surface of the femoral element is convex and laterally has a curved, ammonite-shaped contour with a curvature radius that increases starting from a rear section with a curvature radius R1, a first central section having a curvature radius R2, a second central section having a curvature radius R3, and a front section having a curvature radius R4, with R1≤R2≤R3≤R4.

23 Claims, 4 Drawing Sheets

(52) U.S. Cl.
CPC ............... *A61F 2002/3006* (2013.01); *A61F 2002/30604* (2013.01); *A61F 2002/30672* (2013.01); *A61F 2002/30677* (2013.01); *A61F 2310/00011* (2013.01); *A61F 2310/00179* (2013.01); *A61F 2310/00353* (2013.01)

(58) Field of Classification Search
CPC ............ A61F 2/3836; A61F 2002/3006; A61F 2002/30672; A61F 2002/30677; A61F 2310/00011; A61F 2310/00179; A61F 2310/00353; A61F 2002/30112; A61F 2002/30878; A61F 2/3886
See application file for complete search history.

(56) References Cited

U.S. PATENT DOCUMENTS

| | | | | |
|---|---|---|---|---|
| 6,699,291 | B1* | 3/2004 | Augoyard | A61F 2/3886 |
| | | | | 623/20.24 |
| 2001/0021877 | A1* | 9/2001 | Biegun | A61F 2/3859 |
| | | | | 623/20.28 |
| 2002/0138150 | A1* | 9/2002 | Leclercq | A61F 2/3859 |
| | | | | 623/20.35 |
| 2007/0135926 | A1* | 6/2007 | Walker | A61F 2/3859 |
| | | | | 623/20.31 |
| 2007/0142917 | A1* | 6/2007 | Roche | A61F 2/4081 |
| | | | | 623/19.11 |
| 2008/0172125 | A1* | 7/2008 | Ek | A61F 2/3859 |
| | | | | 623/14.12 |
| 2008/0215157 | A1* | 9/2008 | Earl | A61F 2/4684 |
| | | | | 623/20.35 |
| 2010/0131070 | A1* | 5/2010 | Dees | A61F 2/384 |
| | | | | 623/20.28 |
| 2010/0152319 | A1* | 6/2010 | Shalaby | A61K 9/5026 |
| | | | | 523/117 |
| 2010/0191341 | A1 | 7/2010 | Byrd | |
| 2011/0029092 | A1* | 2/2011 | Deruntz | A61F 2/38 |
| | | | | 623/20.32 |
| 2011/0029093 | A1* | 2/2011 | Bojarski | A61F 2/389 |
| | | | | 623/20.35 |
| 2011/0153026 | A1 | 6/2011 | Heggendorn | |
| 2012/0323337 | A1* | 12/2012 | Parisi | A61F 2/3886 |
| | | | | 623/20.35 |
| 2013/0006373 | A1 | 1/2013 | Wyss | |
| 2015/0134068 | A1 | 5/2015 | Leonard | |
| 2019/0015212 | A1* | 1/2019 | Marlow | A61F 2/389 |
| 2019/0117407 | A1* | 4/2019 | Yang | A61F 2/38 |
| 2019/0159904 | A1* | 5/2019 | Magagnoli | A61F 2/3662 |

FOREIGN PATENT DOCUMENTS

| | | |
|---|---|---|
| WO | 2009105495 | 8/2009 |
| WO | 2016071938 | 5/2016 |

* cited by examiner

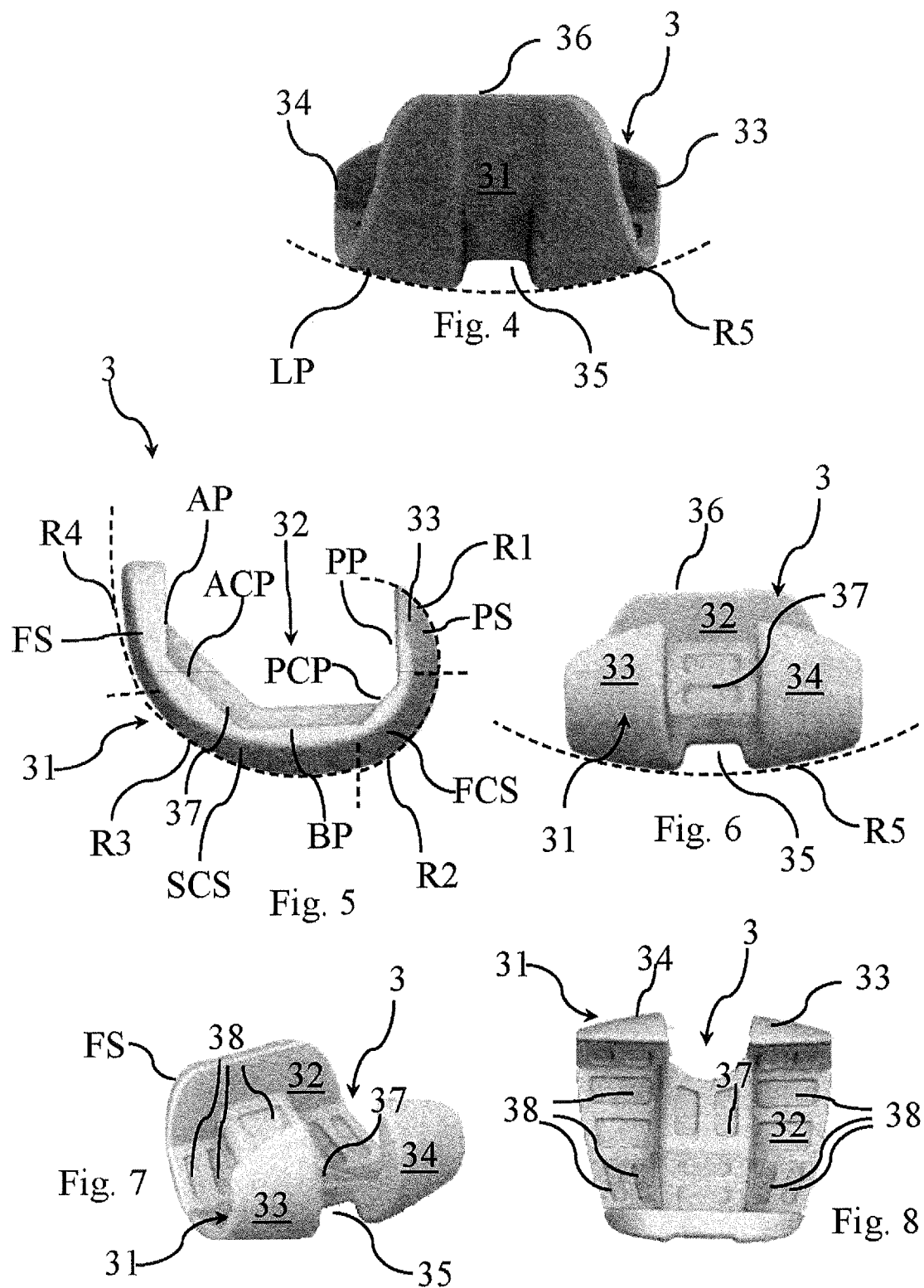

MODULAR SPACER DEVICE FOR THE JOINTS OF THE HUMAN BODY

TECHNICAL FIELD OF THE INVENTION

The present invention refers to a modular spacer device for the temporary substitution of joint prostheses that must be removed, for example following an infection. More particularly, the present invention refers to a spacer device for the knee joint.

STATE OF THE PRIOR ART

In the field of implantology of joint prostheses, it is known that joint prostheses can be susceptible of removal for various reasons, in particular for local infections of the joint after the implant of the prosthesis.

In such case, it is not possible to immediately substitute the infected prosthesis with a new prosthesis, given that the seat of the joint must be treated using suitable antibiotic medications. During the period required for the antibiotic treatment, it is important to maintain the articular space necessary for the implant of a new prosthesis, thus preventing the shortening of the tissues, the atrophying of the joint and the loss of muscle tone. Such technique is known as "two-step implantation" of the joint prostheses.

Temporary articular spacer devices for the knee are known, manually made by the surgeon during the spacer implant surgical operation. Such spacer devices are made of bone cement and are suitably shaped, in a manual manner, immediately before the implant in the articular seat.

The manually-shaped articulated spacer devices suffer from several drawbacks. First of all, the manual process of making the spacer device during the operating session considerably lengthens the duration of the session itself and places the healthcare workers in direct contact with potentially toxic substances used for making the spacer device. In addition, the articular spacer device formed manually can have shape defects that can limit the mobility of the joint.

On the market spacer devices for joints preformed and to be implanted without requiring a manual forming during the surgical operation are available. Nevertheless, such devices have the drawback of being composed of a femoral part and a tibial part having standard sizes and combined with each other a priori, which are thus not always easily adaptable to the anthropomorphic sizes of each patient.

One consequence of the incorrect adaptability of the known spacer devices to the anthropomorphic size of the patient lies in the impossibility of ensuring good mobility of the joint as well as a good resistance of the spacer device itself to the stresses, in particular lateral, to which it is normally subjected during use. It follows that the patient has a poor quality of life while waiting for a new joint prosthesis, and therefore there is the need for a spacer device for joints of the human body which overcomes the aforesaid drawbacks.

OBJECTS OF THE INVENTION

The present invention therefore proposes the technical task of improving the state of the art with regard to the spacer devices for joints of the human body, in particular for the knee joint.

In the scope of such technical task, one object of the present invention is to provide a spacer device for the knee joint which is preformed and which is adapted to the anthropomorphic sizes of each patient to whom it is applied.

A further object of the present invention is to provide a spacer device for the knee joint which is capable of allowing a more suitable and stable movement of the joint with respect to the spacer devices of conventional type.

Another object of the present invention is to provide a spacer device for the knee joint capable of offering greater resistance to lateral thrusts with respect to the spacer devices of conventional type.

In accordance with one aspect of the present invention, a spacer device for the knee joint is provided according to claim 1.

The dependent claims refer to preferred and advantageous embodiments of the invention.

BRIEF DESCRIPTION OF THE DRAWINGS

Further characteristics and advantages of the present invention will be clearer from the detailed but non-exclusive preferred embodiment of a modular spacer device for knee according to the present invention, given as a non-limiting example in the enclosed drawing tables, in which:

FIG. 4 is a front view of the femoral component of the modular spacer device of FIG. 1;

FIG. 5 shows a side view of the femoral component of FIG. 4;

FIG. 6 illustrates a rear view of the femoral component of FIG. 4;

FIG. 7 is a rear perspective view of the femoral component pursuant to FIG. 4;

FIG. 8 shows a plan view of the femoral component of FIG. 4;

EMBODIMENTS OF THE INVENTION

Figure 1:
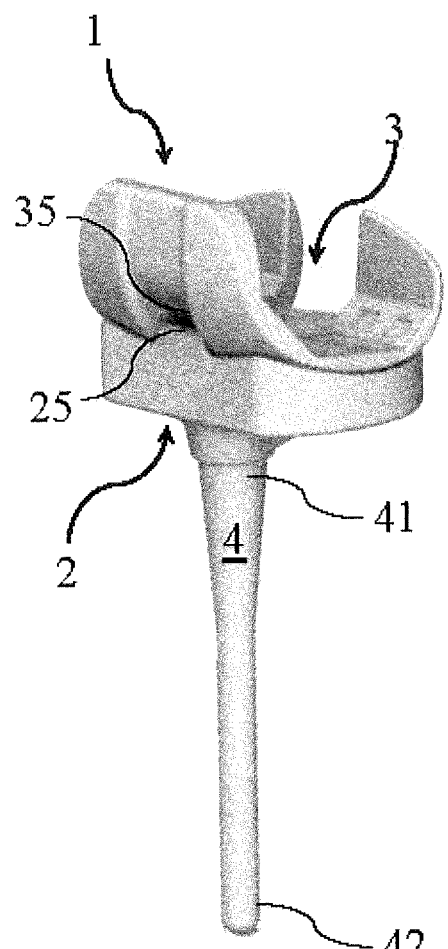
FIG. 1 is a side elevation perspective view of the front of a modular spacer device according to the present invention.
Figure 2:
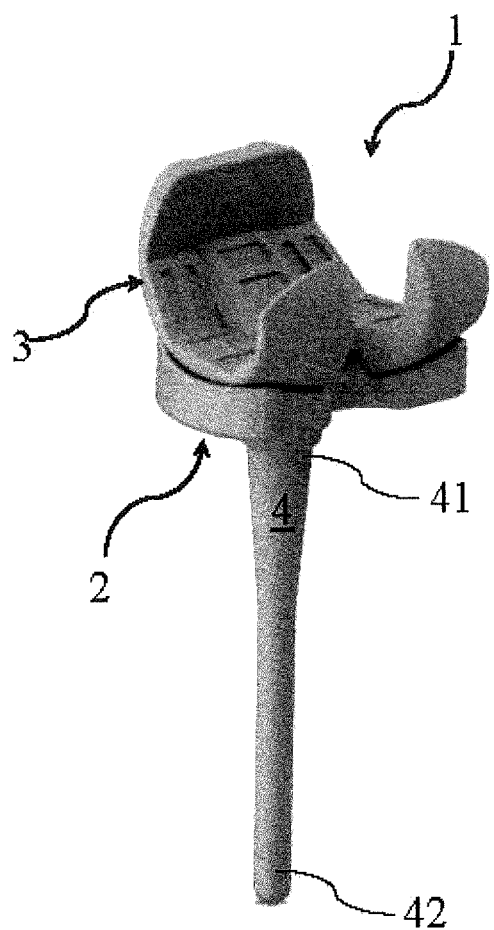
FIG. 2 shows a side elevation perspective view of the rear of the modular spacer device pursuant to FIG. 1.
Figure 3:
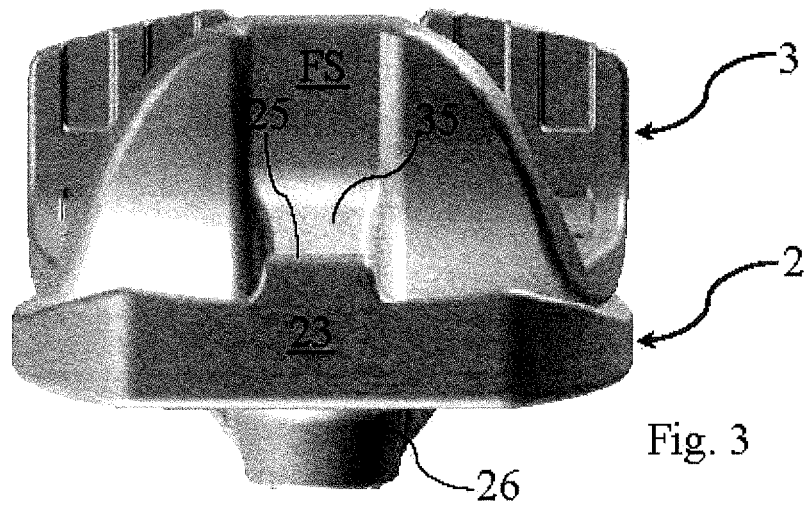
FIG. 3 illustrates a front perspective view, slightly top and in enlarged scale of a femoral component and of a tibial component of the modular spacer device of FIG. 1.
Figure 9:
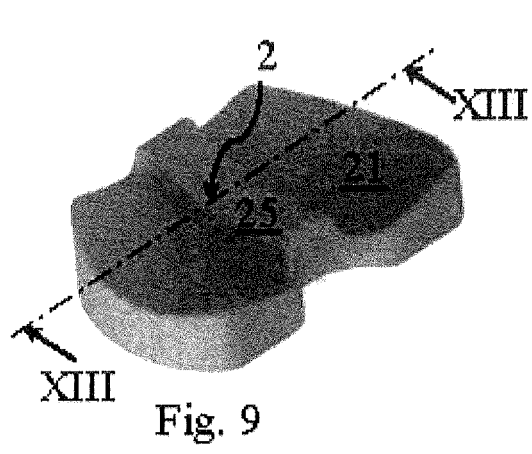
FIG. 9 illustrates a side elevation and rear perspective view of the component of the modular spacer device of FIG. 1.
Figure 10:
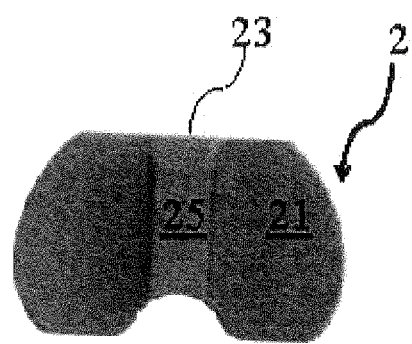
FIG. 10 is a plan view of the tibial component of FIG. 9.
Figure 11:
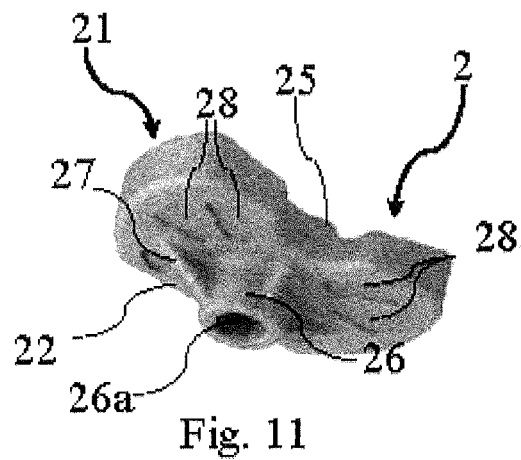
FIG. 11 shows a bottom perspective view of the tibial component of FIG. 9.
Figure 12:
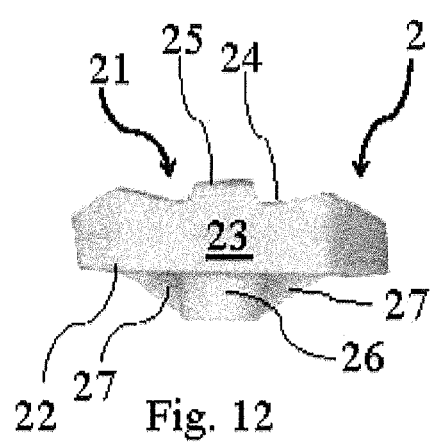
FIG. 12 illustrates a front perspective view of the tibial component of FIG. 9.
Figure 13:
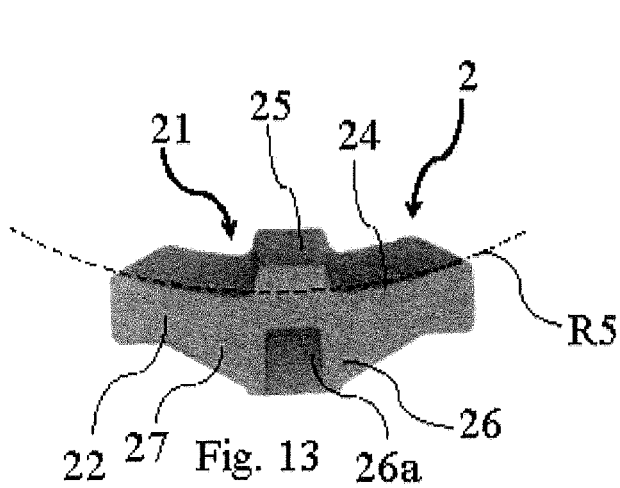
FIG. 13 is a cross section view of the tibial component of FIG. 9, taken along the trace XIII-XIII.
Figure 14:
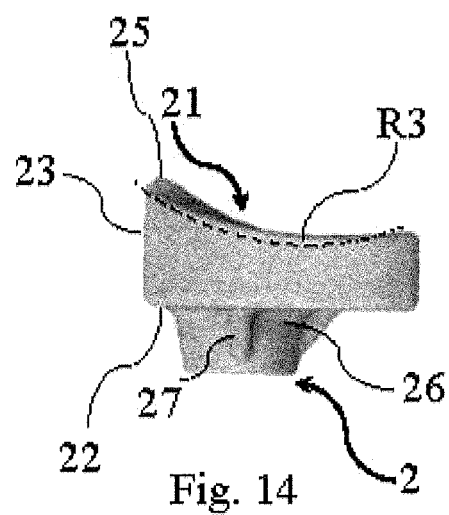
FIG. 14 shows a side view of the tibial component of FIG. 9.

With reference to the enclosed figures, it is observed that a modular spacer device for the knee joint according to the present invention is generically indicated with reference number 1 and comprises at least one tibial element 2, adapted to be constrained to the tibial bone of a patient, at one end of such bone facing the knee joint, and at least one femoral element 3, in turn adapted to be constrained to the femoral bone of the patient, at an end thereof facing the knee joint, and articulated on said tibial element 2.

With particular reference to FIGS. 9 to 14, it will be observed that the tibial element 2 comprises a first surface 21 facing, during use, the femoral element 3 and a second surface 22 opposite thereto. Analogously, with reference in particular to FIGS. 4 to 8, the femoral element 3 has a first surface 31 facing, during use, the respective tibial element 2, and a second surface 32 opposite thereto.

The femoral element 3, as is known, has a substantially C-shaped plan configuration (see FIG. 8), in which each free end of the "C" corresponds with a rear lobe 33, 34 of the femoral element 3.

According to a first aspect of the present invention, the first surface 31 of the femoral element 3 is convex and laterally has (reference is made in particular to FIG. 5) a curved contour of "ammonite" type, in which the curvature radius increases starting from at least one rear section PS having curvature radius R1, towards at least one first central section FCS with curvature radius R2 and at least one second central section SCS with curvature radius R3, up to at least one front section FS of the femoral component 3, which has a curvature radius R4, with R1≤R2≤R3≤R4.

The front section FS of the femoral element 3 frontally has (see the enclosed FIGS. 4 and 6) a substantially curved lower contour LP, more particularly convex, according to a curvature radius R5. The first surface 31 of the femoral element 3 also delimits a central groove 35, extended according to an anteroposterior direction of the femoral element 3, i.e. starting from the front section FS towards the second central section SCS and the first central section FCS of the first surface. Such central groove 35 has a rounded contour. In other words, at such groove 35, the first surface 31 does not have linear or angular progression.

The front section FS of the femoral element 3 has, seen frontally (see FIG. 4), an upper contour 36 substantially curved according to a substantially bell-shaped pattern.

Figure 15:
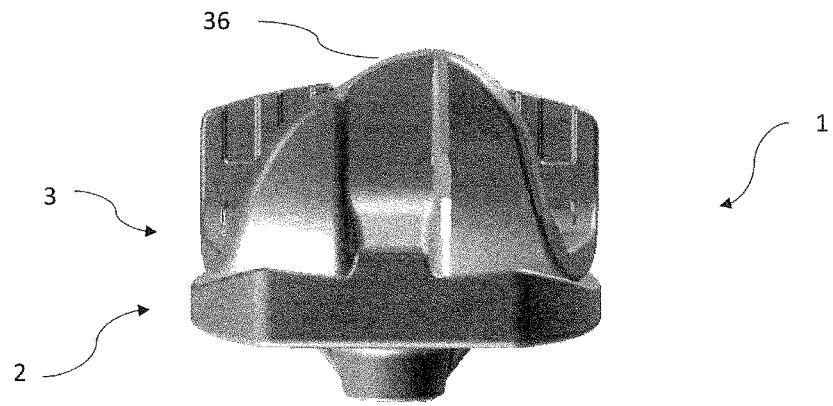
FIG. 15 is a front view of a version of the modular spacer device of FIG. 3.
Figure 16:
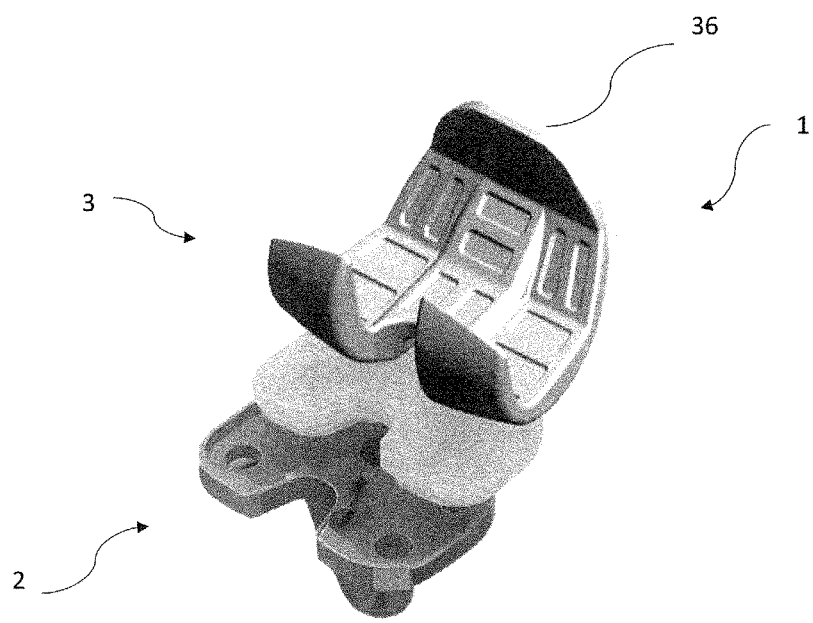
FIG. 16 is a top rear perspective view of a version of the modular spacer device according to the present invention.

In one version of the invention, illustrated for example in FIGS. 15 and 16, the upper contour 36 of the front section FS of the femoral element 3 has a tilted contour, sloping to the left (as is visible for example in FIG. 15) or to the right. In such a manner, the femoral element 3 of the modular spacer device 1 according to the present invention can be adapted respectively for a left knee or for a right knee. Such femoral component 3 can be coupled, as will be better indicated hereinbelow, to a left, right or symmetric tibial element 2.

According to a further aspect of the present invention, the second surface 32 of the femoral element 2 of the modular spacer device 1 is concave and laterally has (reference is made to FIG. 5 in particular) a curved U-shaped contour comprising at least one rear portion PP and one front portion AP parallel to each other, a base portion BP, substantially orthogonal to said rear portion PP and to said front portion AP, a rear connecting portion PCP, between said rear portion PP and said base portion BP, as well as a front connecting portion ACP, between said front portion AP and said base portion BP.

The rear connecting portion PCP and the front connecting portion ACP can be curved or they can have substantially rectilinear configuration and are arranged, in the latter case, obliquely with respect to the portions to which they are respectively connected.

With one such configuration, each of the rear lobes 33 and 34 of the femoral element 3 is delimited between at least one rear portion PP and one rear connecting portion PCP of the second surface 32 and at least one rear section PS with curvature radius R1 and a first central section FCS with curvature radius R2 of the first surface 31 of the femoral element 3.

The femoral element 3 of the modular spacer device 1 according to the invention has an element in relief or central rib 37 with anteroposterior development, at the base portion BP and at the front connecting portion ACP on the second surface 32. Such central rib 37 is arranged at the central groove 35 made on the first surface 31 of the femoral element 3. The central rib 37, like the corresponding central groove 35, also has a rounded contour. In other words, at the central rib 37, the second surface 32 does not have linear or angular development.

With reference now to the tibial element 2 of the modular spacer device 1 according to the invention, this has a substantially reversed-"U" plan configuration (see FIG. 10), in which the base portion of the "U" corresponds to a front portion (front during use) 23 of the tibial element 2 and has a substantially rectilinear pattern.

According to one aspect of the present invention, the first surface 21 of the tibial element 2 is concave and laterally has (reference is made to FIG. 14) a curved contour, more particularly concave, substantially complementary to the pattern of the second central section SCS with curvature radius R3 of the corresponding femoral component 3.

Such first surface 21, in one version of the invention, also frontally has (see in particular FIG. 13) a substantially concave contour 24 corresponding to the substantially curved lower contour LP with curvature radius R5 of the femoral element 3.

In a further version of the invention, the first surface 21 can frontally have a substantially flat or concave contour 24, though with very large curvature radius (e.g. much larger than R5) such to make it appear substantially flat. Also in such version, the first surface 21 acts as a support and is articulated with the substantially curved lower contour LP with curvature radius R5 of the femoral element 3.

In addition, in a further version of the invention, the first surface 21 can have a contour 24 of non-symmetric type, in the sense that the contour 24, in its medial portion, can have a concave pattern and in its lateral portion can have a flat contour, or vice versa, in accordance with the specific anatomic needs of the patient. According to this version, the tibial element 2 has a "left" or "right" contour in accordance with the location of the concave portion. In all cases, the contour 24 allows the abutment and the articulation with the substantially curved lower contour LP with curvature radius R5 of the femoral element 3.

In addition, the first surface 21 of the tibial element 2 delimits a relief portion or central rib 25 with rounded contour (as in the sense described above with reference to the central groove 35 and the central rib 37 of the femoral element). Such relief portion or central rib 25 is extended according to an anteroposterior direction in the tibial element 2 and has a configuration such to be substantially insertable to size in a corresponding central groove 35 delimited in the femoral element 3.

According to one particularly preferred aspect of the present invention, the rib 25 of the tibial element 2 projects upward or stands out from the rest of the first surface 21 in a very pronounced manner, for example it projects upward for about 0.8-1.2 cm with respect thereto or, more preferably, for about 10 mm.

In some applications, when the knee joint is particularly compromised, such as in the case of a second prosthesis replacement with removal of the lateral ligaments, the rib 25 can be higher, up to and over 20 mm.

The central rib 25, as will be easy to understand, acts as a stabilizer means in the sense that it prevents lateral movements between the femoral element 3 and the tibial element 2, once they have been coupled together as described above. In any case, the central rib 25 and the central groove 35 are sized in a manner such that there is a certain clearance between them, such that the femoral element 3 can be moved, in the sense that will be clearer hereinbelow, in anteroposterior direction with respect to the tibial element 2.

With one such configuration of the central rib 25 of the tibial element 2 and of the central groove 35 of the femoral element 3, the man skilled in the art will have no difficulty in understanding that the femoral element of the modular spacer device 1 according to the invention can be articulated on the corresponding tibial element 2. Indeed, the femoral element 3, more particularly its convex first surface 31, during use can roll and partially translate with respect to the concave first surface 21 of the tibial element 2, even if maintaining a high lateral stability due to the particular sizing of the central rib 25 and of the corresponding central groove 35.

Such rolling and partially translational motion is due to the configuration of "ammonite" type of the femoral element 3 and of the corresponding configuration of the tibial element 2.

Returning to the tibial element 2 of the modular spacer device according to the invention, this has the second surface 22 substantially flat and connected (in any suitable manner), in a central region corresponding to the central rib 25 of the first surface 21, to an engagement means 26. Such engagement means 26 is employed for engaging the tibial element 2 to a bone end of a patient.

According to one variant of the modular spacer device 1 according to the present invention, the modular spacer device optionally comprises at least one stem 4 engageable, for example via shape coupling, with the tibial element 2 at the engagement means 26.

According to a preferred variant of the invention, the engagement means 26 is a sleeve element, fixed to the second surface 22 of the tibial element 2 with its longitudinal symmetry axis substantially orthogonal to such surface 22. In this manner, the sleeve element delimits a housing seat 26a for one end of the stem 4.

The tibial element 2 also comprises a plurality of reinforcement tabs 27 (see FIGS. 11 to 14) between the second surface 22 and the sleeve element 26, designated to make the structure itself of the tibial element 2 more rigid.

The stem 4 has a first end 41, insertable to size in the seat 26a delimited by the engagement means or sleeve 26, and has a longitudinal pattern tapered towards the other end 42 thereof, intended to be inserted, if provided, in the tibial bone cavity of a patient.

Well, according to a preferred variant of the invention, both the femoral element 3 and the tibial element 2 can have plan extension that differs in accordance with the various predetermined formats or sizes, but they also maintain the configuration—i.e. the size and shape—constant (i.e. independent of the format or size) respectively of the central groove 35 and of the central rib 25, and/or of the curvature radii R3 and R5.

In this manner, the tibial element 2 and the femoral element 3 of the modular spacer device according to the invention can always be coupled together at the respective first surfaces 21 and 31, independent of the respective formats or respective sizes.

Moreover, the central rib 25 of the tibial element 2 and the central groove 35 of the femoral element are configured in a manner such that, if during the movement of the knee joint the device sustains lateral thrust stresses, the central rib 25 maintains the femoral element 3 in the seat, ensuring a correct movement and a good stability of the articulation.

The lateral stability of the modular spacer device according to at least one version of the invention is furthermore also due to the particular convex or "ammonite" contour of the first surface 31 of the femoral element 3 and due to the corresponding concave or "sunken" contour of the corresponding first surface 21 of the femoral element. Their particular configuration, together with the configuration of the central rib 25, which is raised with respect to the rest of the first surface 21 in a much more pronounced manner with respect to the devices of conventional type, ensures that the femoral stress forces result in a self-centering moment, i.e. of longitudinal alignment between the femoral element 3 and the tibial element 2, hence offering a resistance to the lateral forces that is decidedly higher with respect to the modular spacer devices of conventional type.

The different formats or sizes of the tibial element 2 and of the femoral element 3 are interchangeable with respect to each other, due to the equivalence of the curvature radii R3 and R5 of the first surfaces 31 and 21 and/or since the first surfaces 31 and 21 can be coupled together. Such modularity of the spacer device 1 therefore allows adapting it to the anthropomorphic sizes of the femoral and tibial ends of each patient, which can be different from each other.

The configuration of the curvature radii R3 and R5 allows obtaining a relative main rolling motion between the femoral element 3 and the tibial element 2 as well as a partial sliding motion therebetween.

Such main rolling motion between the first surface 31 of the femoral element 3 and the first upper surface 21 of the tibial element 2 allows the patient to complete a bending and extension movement of the articulation similar to the normal physiological movement of the knee joint.

With one such configuration, the man skilled in the art will have no difficulty observing that, in order to be able to adapt the modular spacer device 1 to the sizes of each patient, the surgeon is not required to carry out any manual modification operation for the femoral element 3 and the tibial element 2, thus reducing the times necessary for the implant of the modular spacer device 1. Indeed, the surgeon is only requested to select, from among the various available formats and sizes and for each element that composes the modular spacer device 1, the size or format that is best adapted to the actual size of the respective anatomic seat of the patient, without having to use a tibial element and a femoral element of the same size.

In order to ensure that the surgeon has maximum freedom of selection, the femoral element 3, the tibial element 2 and the stem 4 will be packaged in separate packages and in a single size.

In a manner entirely analogous to that described above, the tibial element 2 and the stem 4 always maintain constant (independent of their format or size) the configuration—i.e. the size and shape—respectively of the engagement means 26 (in particular the housing seat 26a) and of the connection end 41. In this manner, also the tibial element 2 and the stem 4 can be coupled together, independent of the plan extension of the tibial element 2 and of the cross section of the stem 4.

The different configurations of the femoral element 3, of the tibial element 2 and of the stem 4, compatible with each other, ensure a high modularity to the modular spacer device 1.

In particular, the femoral element 3 is shaped in a manner such to be coupled with any size of the tibial element 2 in order to adapt the sizes of the modular spacer device with the sizes of the bone ends to which it must be connected.

Therefore, the surgeon will have a wide selection of formats for the femoral element 3 and the tibial element 2 and will not be obliged to select femoral and tibial elements of the same format or size. In addition, the selection will be even greater given the possibility of deciding whether he/she wishes to use the stem 4 or not.

With one such configuration, the above-described modular spacer device allows obtaining a high mobility of the knee joint and a movement similar to that of a natural articulation, even in the presence of different anatomic sizes, between the different articular portions of a patient.

Well, according to another preferred aspect of the present invention, in the second surface 32 of the femoral element 3 and/or in the second surface 22 of the tibial element 2, at least one bas-relief or recess is obtained, of plan extension much greater than the respective depth. It is observed that, in the case represented in the figures (see in particular FIGS. 7, 8 and 11), the bas-relief zones are present both on the tibial element 2 and on the femoral element 3 and are respectively indicated with the reference numbers 38 and 28.

Such bas-relief zones 38 and/or 28 provided on the femoral element 3 and/or on the tibial element 2 are provided for facilitating the adhesion of the respective femoral component 3 and/or tibial component 2 to the corresponding bone end, by means of the use of a filling material, specifically bone cement and/or any other suitable material, during the surgical procedure of implant of the modular spacer device 1.

The arrangement thereof, such as their extension, can vary as a function of specific needs, for example as a function of the format or size of the femoral element 3 and of the tibial element 2.

The bas-relief zones 38 and/or 28 form seats for housing a filling material as stated above, which—according to one aspect of the present invention—can be self-hardening or solidifiable.

In one version of the invention, the filling material can be prepared by the surgeon during the operating procedure and/or it can lack pharmaceutical or medical substances and/or it can be admixed therewith based on the selection of the surgeon and on the needs of the patient.

If the filling material also comprises at least one pharmaceutical or medical substance, the bas-relief zones 38 and/or 28 in practice act as a tank for storing such pharmaceutical or medical substance to be released within the human body, more particularly in the bone or articular seat where the modular spacer device 1 is implanted.

Naturally, the pharmaceutical or medical substance, such as at least one antibiotic, inserted in the filling material is of soluble type, and therefore is released towards the bone tissue adjacent to or in contact with the filling material in order to heal or at least prevent the infection thereof.

In one version of the invention, the filling material is non-reabsorbable or non-degradable in the human body at least for the stay time of the spacer device within the human body itself. The filling material is thus permanent.

In one version of the invention, the filling material is applied by the surgeon before the implant of the modular spacer device itself.

In a further version of the invention, the aforesaid filling material can thus comprise at least one pharmaceutical or medical substance already arranged in the material, which constitutes the filling material itself, and it may, in preparation step, be admixed with a further substance.

According to one aspect of the present invention, the filling material, by virtue of the step of preparation or solidification to which it is subjected, can be porous.

The size of the pores of the filling material (and/or of the material constituting the femoral element 3 or the tibial element 2 of the spacer device) is, in any case, such to prevent bone growth from occurring within the same during use, and hence to prevent such growth within the modular spacer device 1 according to the invention, which as stated is temporary.

One such configuration of the pores therefore facilitates the subsequent removal of the spacer device itself from the treated bone or articular seat, once its treatment function as been completed.

By way of example, the pores can have, in one version, average size of less than 100 micron.

The spacer device 1 is configured in a manner such that when, during use, it is implanted in the human body, the filling material in the bas-relief zones 38 and/or 28 is in contact with the bone tissues to be treated.

According to one version, the filling material is flush with the respective second surface 32 and/or 22 of the respective femoral element 3 or tibial element 2.

According to a further version, the filling material exits from the respective bas-relief zone 38 and/or 28 and therefore projects with respect to the second surface 32 and/or 22 of the respective femoral element 3 or tibial element 2.

The overall volume of the bas-relief zones 38 and/or 28 respectively on the femoral element 3 and/or on the tibial element 2 and the quantity of filling material is thus suitable for the time period estimated for treating the infection underway in the seat where the modular spacer device 1 according to the invention is implanted.

According to one aspect of the present invention, the bas-relief zones 38 and/or 28 define, along the respective second surfaces 32 and 22, an open-cell structure.

More in detail, the open-cell structure comprises a plurality of cells side-by-side each other, each corresponding with a bas-relief zone 38 and/or 28. According to one version, the bas-relief zones 38 and/or 28 are adjacent to each other on the respective femoral 3 and/or tibial elements 2.

The cells can be more or less spaced from each other depending on the format of the respective femoral element 3 or tibial element 2 and in a manner such that these are not situated at portions of the device that, during use, are subjected to greater mechanical stresses, for example wear, bending, fatigue, etc.

As already mentioned above, the plan extension of each bas-relief zone 38 and/or 28 is much greater than the respective depth. In such a manner, among other things, the surgeon will be facilitated in the application of the above-described filling material in the bas-relief zones 38 and/or 28.

According to a further aspect of the invention, the tibial element 2, the femoral element 3 and, if provided, the stem 4 are preformed in various formats or sizes and are made of biologically compatible material, possibly porous.

Such biologically compatible material can be selected from among plastic materials, possibly thermoformable, such as polymethylmethacrylate (PMMA), polyvinylchloride (PVC), polystyrene (PS), polyethylene (PE), ultra-highmolecular-weight polyethylene (UHMWPE), high or low density polyethylene, etcetera, or non-polymeric materials, ceramics, metals, metal alloys, organometallic compounds, and/or a combination of the same.

As is visible in one version of the invention illustrated in FIG. 16, the tibial element 2 can be made of two pieces, which once assembled together recreate the above-described tibial element 2 and the constituent surfaces. Such two pieces can be made of materials that are different from each other, selected from among those listed above, for example in order to increase the slidability of the femoral element 3 on the tibial element 2.

In one version of the present invention, the biologically compatible material is a bone cement with polymethylmethacrylate (PMMA) base.

In another version of the invention, the aforesaid biologically compatible material initially lacks pharmaceutical or medical substances.

In a further second version, the aforesaid biologically compatible material comprises at least one pharmaceutical or medical substance.

According to a further version of the present invention, the biologically compatible material can be a ceramic cement, such as calcium sulfate known as plaster or $CaSO_4$, which in addition to solidifying in reduced times is able to release calcium ions.

In order to make elements of the modular spacer device 1 according to the invention, further materials of biocompatible type can nevertheless be used, with respect to that described above, without departing from the protective scope of the present invention.

The invention described above attains numerous advantages.

The femoral 2 and tibial 3 elements, being preformed in various sizes, simplify the steps of implant thereof in the articulation seat, since they do not require further operations of forming or modifications of their sizes so to adapt them to the sizes of the bone ends. With a modular spacer device 1 as described above, the time necessary for the execution of the surgical intervention is reduced and the patient can have each part of the modular spacer device 1 perfectly suitable for his/her actual bone and anatomic structure and/or in order to make up for possible deficiencies due to pathological and/or surgical situations to which the patient is subjected.

Additionally, the particular configuration of the central groove 35 of the femoral element 3 and of the central rib 25 of the tibial element 2, which stands out in a more pronounced manner from the first surface 21 with respect to the conventional devices, and the particular "ammonite" convex contour of the first surface 31 of the femoral element 3 and/or the corresponding concave or "sunken" contour (at least according to one version of the invention) of the corresponding first surface 21 of the femoral element, provide a resistance to the lateral thrusts that is decidedly higher with respect to the modular spacer devices of conventional type, since the femoral stress forces result in a self-centering moment, i.e. of longitudinal alignment between the femoral element 3 and the tibial element 2.

The possibility of pre-impregnating or impregnating the modular spacer device 1 by using pharmacological and/or therapeutic products allows treating the local infections in the articulations seat and attaining optimal conditions for the implant of a new joint prosthesis.

The invention thus conceived is susceptible of numerous modifications and variants, all falling within the scope of the inventive concept.

In addition, all details can be substituted with other technically equivalent elements. In practice, the materials used, as well as the contingent shapes and sizes, can vary in accordance with requirements without departing from the protective scope of the following claims.

Thus, for example, in a manner entirely analogous to the stem 4 of the above-described modular spacer device 1, a stem or shank can also be provided for the connection between the femoral component 3 of the modular spacer device according to the invention and the femoral bone end. Such shank or stem can be of any suitable type, for example like that provided for the tibial element 2. In this case, the femoral element 3 will comprise engagement means on the respective second surface 32 for the connection to such stem or shank.

The femoral element 3 and the tibial element 2 can be made in a single piece or obtained by means of welding of multiple components.

The invention claimed is:

1. A modular spacer device (1) for a knee joint, comprising:
    a tibial element (2) adapted to be constrained to a tibial bone, at one end of said tibial bone facing the knee joint, and
    a femoral element (3), adapted to be constrained to a femoral bone, at one end of a femur facing the knee joint, and articulated onto said tibial element (2),
    wherein said tibial element (2) comprises a first surface (21) facing said femoral element (3) and a second surface (22) opposite thereto, and said femoral element (3) comprises a first surface (31) facing said tibial element (3) and a second surface (32) opposite thereto,
    wherein said femoral element (3) has a "C"-shaped plan configuration,
    wherein each free end of the "C"-shaped plan configuration delimits a rear lobe (33, 34) of said femoral element (3),
    wherein said first surface (31) of said femoral element (3) is convex and has a curved, ammonite shaped contour with a curvature radius that increases along an entire lateral profile of the first surface that begins at a rear section (PS) having a first curvature radius (R1), and continues along a first central section (FCS) contiguous to the rear section and having a second curvature radius (R2), along a second central section (SCS) contiguous to the first central section and having a third curvature radius (R3), and along a front section (FS) of said femoral element (3) contiguous to the second central section and having a fourth curvature radius (R4), and
    wherein said front section (FS) of said first surface (31) of said femoral element (3) presents frontally a convex lower contour (LP) extending along an entire frontal width of said femoral element and having a fifth curvature radius (R5) and delimits a central groove (35) extending in an anterior-posterior direction along an entirety of said femoral element (3).

2. The modular spacer device according to claim 1, wherein said front section (FS) of said first surface (31) of said femoral element (3) frontally has a curved upper contour (36) with a bell-shaped pattern or a pattern having a lateral inclination.

3. The modular spacer device according to claim 1, wherein said second surface (32) of said femoral element (3) is concave and laterally presents a curved U-shaped contour, comprising a rear portion (PP) and a front portion (AP) parallel to each other, a base portion (BP) orthogonal to said rear portion (PP) and to said front portion (AP), a rear connecting portion (PCP) between said rear portion (PP) and said base portion (BP), and a front connecting portion (ACP), between said front portion (AP) and said base portion (BP).

4. The modular spacer device according to claim 3, wherein one or both of said rear connecting portion (PCP) and said front connecting portion (ACP) are curved or have a rectilinear configuration and are each disposed obliquely between the respective portions (BP, PP and/or BP, AP) to which they are respectively connected.

5. The modular spacer device according to claim 3, wherein each of the rear lobes (33, 34) of said femoral element (3) is delimited between said rear portion (PP) and a rear connecting portion (PCP) of said second surface (32), and said rear section (PS) has the first curvature radius (R1) and the first central section (FCS) has the second curvature radius (R2) of said first surface (31) of said femoral element (3).

6. The modular spacer device according to claim 3, wherein said femoral element (3) includes a central rib (37) having anteroposterior development at said base portion (BP) and said front connecting portion (ACP) on said second surface (32) and at said central groove (35) of said first surface (31).

7. The modular spacer device according to claim 1, wherein said tibial element (2) presents a reversed "U" plan configuration, wherein a base portion of the "U" corresponds to a front section (23) of said tibial element (2) and is a rectilinear portion.

8. The modular spacer device according to claim 1, wherein said first surface (21) of said tibial element (2) is concave and laterally has a curved contour matching a development of said second central section (SCS) having the third curvature radius (R3) of said femoral element (3).

9. The modular spacer device according to claim 1, wherein said first surface (21) of said tibial element (2) is concave and frontally has a concave upper contour (24) corresponding to said convex lower contour (LP) having the fifth curvature radius (R5) of said femoral element (3), or wherein said first surface (21) of said tibial element (2) is concave and frontally presents a flat upper contour (24) designed to articulate with said convex lower contour (LP) with the fifth curvature radius (R5) of said femoral element (3), or wherein said first surface (21) of said tibial element (2) is concave and frontally presents an upper contour (24) having a flat medial or lateral portion and a concave lateral or medial portion, and wherein said flat upper contour (24) is designed to articulate with said convex lower contour (LP) with the fifth curvature radius (R5) of said femoral element (3).

10. The modular spacer device according to claim 1, wherein said first surface (21) of said tibial element (2) delimits a central rib (25) extending in an anteroposterior direction into said tibial element (2) and configured such that said central rib is insertable to size, with a reduced clearance, into said central groove (35) delimited into said femoral element (3), said central rib (25) being concave in the anteroposterior direction.

11. The modular spacer device according to claim 10, wherein said central rib (25) projects upward from a rest of the first surface (21) for 0.8-1.2 cm, up to 2 cm, or more than 2 cm.

12. The modular spacer device according to claim 10, wherein said second surface (22) of said tibial element (2) is flat and presents, in a central region corresponding to the central rib (25) of the first surface (21) an engagement element (26) adapted to engage said tibial element (2) to a patient bone end.

13. The modular spacer device according to claim 12, further comprising at least one stem (4) engageable with said tibial element (2) at said engagement element (26).

14. The modular spacer device according to claim 13, wherein said at least one stem (4) has a first end (41) adapted to be coupled by shape coupling with said at least one engagement element (26), and further has a longitudinal development tapered toward one end (42) opposed to said first end (41).

15. The modular spacer device according to claim 14, wherein said femoral element (3) and said tibial element (2) have different plan extensions, depending on formats or sizes, but always keep constant, independently from their format or size, a dimension and a configuration of said central groove (35) and said central rib (25), or said third and fifth curvature radii (R3) and (R5), thereby resulting connectable with each other, at the respective first surfaces (31, 21), independently from the respective plan extensions.

16. The modular spacer device according to claim 15, wherein said first surface (31) of said femoral element (3) is in revolving and partially translatable contact with said first surface (21) of said tibial element (2).

17. The modular spacer device according to claim 15, wherein said tibial element (2) and said stem (4) are adapted to be coupled with each other at the engagement element (26) of said tibial element, independently from the plan extension of said tibial element (2) and a cross-section of said stem (4).

18. The modular spacer device according to claim 14, wherein said tibial element (2), said femoral element (3) and, if provided, said stem (4) are preformed and made of a biologically compatible material.

19. The modular spacer device according to claim 18, wherein said biologically compatible material is porous.

20. The modular spacer device according to claim 19, wherein said biologically compatible material comprises at least one of the following materials: plastic materials, or non-polymeric materials, ceramics, metals, metal alloys, organometallic compounds, or a combination thereof.

21. The modular spacer device according to claim 19, wherein said porous biologically compatible material is adapted to be pre-impregnated with pharmaceutical and therapeutic products.

22. The modular spacer device (1) according to claim 19, wherein said porous biologically compatible material is originally devoid of medical substances and is designed to be impregnated with pharmaceutical and therapeutic products before implantation.

23. The modular spacer device according to claim 1, wherein at least one bas-relief area (38 and/or 28) is defined in said second surface (32) of one or both of said femoral element (3) or said second surface (22) of said tibial element (2), and has a plan cross-section larger than a respective depth.

* * * * *